(12) United States Patent
Grey

(10) Patent No.: US 7,089,061 B2
(45) Date of Patent: Aug. 8, 2006

(54) DEVICE AND METHOD FOR NAUSEA SUPPRESSION

(75) Inventor: Thomas L. Grey, Carlsbad, CA (US)

(73) Assignee: Abbott Laboratories, Abbott Park, IL (US)

( * ) Notice: Subject to any disclaimer, the term of this patent is extended or adjusted under 35 U.S.C. 154(b) by 94 days.

(21) Appl. No.: 10/229,596

(22) Filed: Aug. 27, 2002

(65) Prior Publication Data

US 2004/0127939 A1    Jul. 1, 2004

(51) Int. Cl.
*A61N 1/08*    (2006.01)

(52) U.S. Cl. .............................. 607/63; 607/72; 607/48; 606/41

(58) Field of Classification Search .................. None
See application file for complete search history.

(56) References Cited

U.S. PATENT DOCUMENTS

| 4,981,146 | A | * | 1/1991 | Bertolucci .................... 607/72 |
| 4,982,432 | A | * | 1/1991 | Clark et al. .................. 704/271 |
| 5,067,478 | A |   | 11/1991 | Berlant |
| 5,092,344 | A |   | 3/1992 | Lee |
| 5,405,357 | A | * | 4/1995 | Rowe-Lanzisera et al. . 606/204 |
| 6,076,018 | A | * | 6/2000 | Sturman et al. .............. 607/72 |
| 6,567,990 | B1 | * | 5/2003 | Spitznagle .................. 2/161.7 |
| 6,595,918 | B1 | * | 7/2003 | Gopinathan et al. ........ 600/300 |

FOREIGN PATENT DOCUMENTS

WO        02/41942        5/2002

* cited by examiner

*Primary Examiner*—Glenn K. Dawson
(74) *Attorney, Agent, or Firm*—David L. Weinstein

(57) ABSTRACT

A nausea control device which provides electrical stimulation to the K9 acupressure point or points on the finger of a patient. Various mounting structures may be used to hold the electrodes in place over the K9 point, and hold the pulse generation circuitry and power supply in convenient location relative to the electrodes and the patient.

7 Claims, 4 Drawing Sheets

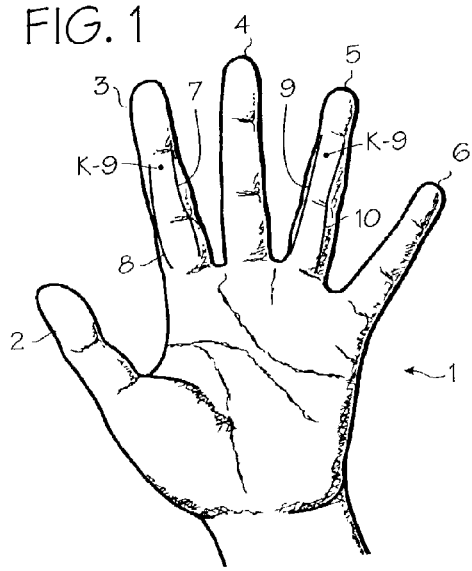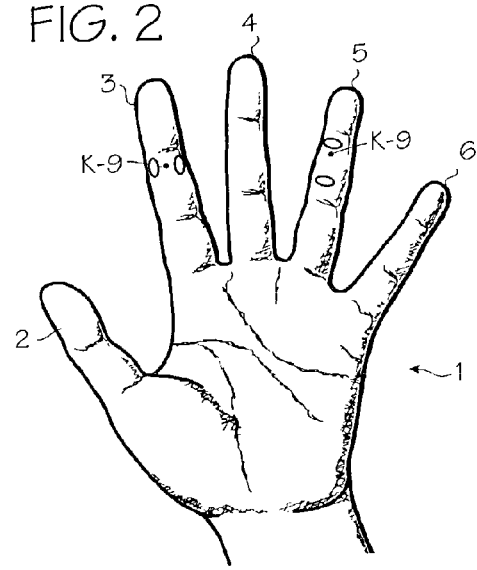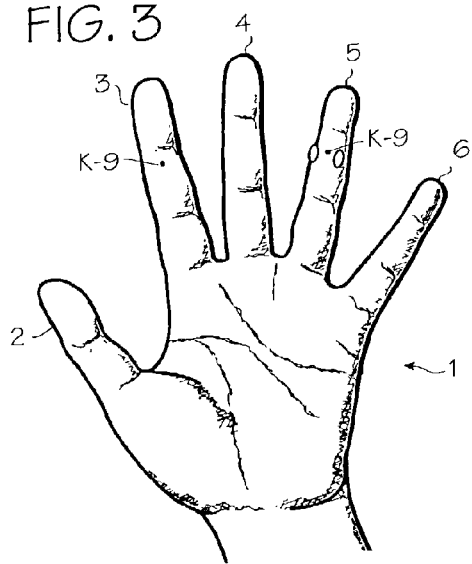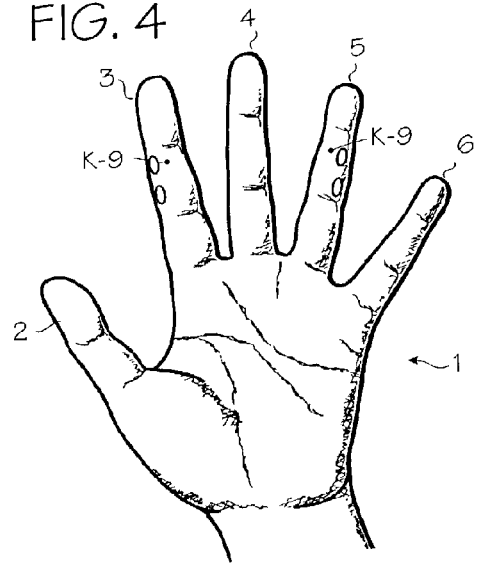

DEVICE AND METHOD FOR NAUSEA SUPPRESSION

FIELD OF THE INVENTIONS

The inventions described below relate the field of electro-acupuncture and nausea control.

BACKGROUND OF THE INVENTIONS

Woodside Biomedical, Inc. currently markets a wrist-borne nausea control device under the trademark RELIEF-BAND®. The device is effective in alleviating the nauseous symptoms of motion sickness, morning sickness, anesthesia drugs and chemotherapy drugs. The device applies pulses of electrical stimulation to a specific point on the wrist, referred to as the P6 acupuncture point. The treatment provided by the device is sometimes referred to as electro-acupuncture, which is a form of acupuncture, and the ventral site of application is referred to in the acupuncture art as the P6 point, pericardium 6 point, or master point of the pericardium meridian (sometimes referred to as the vascular meridian). It is also portable, self-contained and convenient to the patient. Electrical pulse repetition rate of approximately 70 pulses per second and a pulse width of 80 microseconds have been found to provide effective relief of nausea in a patient. Our currently preferred electrical pulse pattern comprises about 350 microsecond pulse width at about 31 pulses per second at power levels of about 10–35 milliamps peak pulse height. Thus a wide range of pulse patterns may be used in non-invasive nerve stimulation devices.

Recently, the K9 Korean acupressure point has been identified as a point that may be manually stimulated to relieve post-operative nausea. Initial testing of electrical stimulation of the K-9 acupressure point indicates that it will alleviate nausea.

SUMMARY

The devices and methods described below provide for convenient and effective application of electrostimulation to the K9 acupressure point. In different embodiments, pairs of electrodes are mounted on the K9 points, or closely overlying the K9 point, of the index finger, ring finger, or both, and electrical stimulation is provided through the pad of the finger to the K9 point. Several means for mounting the electrodes to the proper point on the finger, and for conveniently housing the necessary pulse generation circuitry and power source, may be used in combination with the electrodes. The electrodes may be mounted on a ring, finger clip, or glove, for example, and the pulse generation circuitry can be placed relative to the mounting structure to minimize its interference with activities of the user.

BRIEF DESCRIPTION OF THE DRAWINGS

FIG. 1 shows the position of the K-9 acupressure points on the hand.

FIG. 2 shows the placement of electrodes relative to the K9 points, with the electrodes arranged longitudinally relative to the fingers.

FIG. 3 shows the placement of electrodes relative to the K9 points, with the electrodes arranged laterally on the fingers.

FIG. 4 shows the placement of electrodes relative to the K9 points, with the electrodes arranged longitudinally over the course of digital nerves on the fingers.

DESCRIPTION OF THE INVENTIONS

Figure 5:
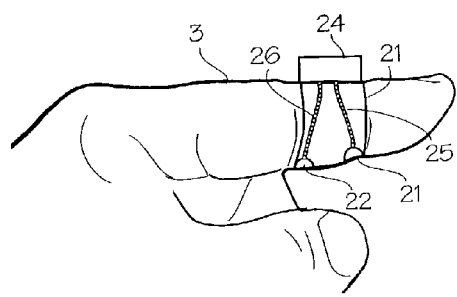
FIG. 5 shows a ring adapted to carry the electrodes used to stimulate the K9 points.

FIG. 1 shows the position of the K-9 acupressure points on the hand and illustrates the anatomical structures and landmarks useful in describing the devices and methods. The figure shows the hand 1 of a patient in the palmar view, and the thumb 2, index finger 3, the middle finger 4, the ring finger 5, and the pinky 6. One K-9 point is located on the palmar side of the index finger, on the pad of the second phalange of the index finger. One K-9 point is located on the palmar side of the third finger (the ring finger), on the pad of second phalange of the third finger. The points are just proximal of the head of the middle phalange of each finger. These points may be stimulated with electrical pulses, applied with surface mounted electrodes placed in a position closely overlying the K-9 point. The palmar digital nerves 7 and 8 on the index finger, and the palmar digital nerves 9 and 10 on the ring finger, run superficially along the radial and ulnar sides of the palmar surface of the fingers (all four fingers have these nerves).

FIG. 2 shows the placement of a pair of electrodes relative to the K9 point on the ring finger, with the electrodes arranged longitudinally relative to the fingers. One electrode is placed distal to the K-9 point, and the other electrode is placed proximal to the K9 point. The electrodes are operated as a bipolar pair, with one electrode serving as a source of a simulation pulse and the other electrode serving as ground, and preferably the stimulation pattern is bi-phasic in the sense that pulses of negative and positive polarity are applying alternately.

The electrodes may be placed in lateral relationship relative one of the K-9 points, as shown in FIG. 3. One electrode is placed laterally to the K-9 point (on the ulnar side), and a second electrode is placed medially to the K-9 point (on the radial side). Though the K-9 point of the index fingers is illustrated with laterally placed electrodes and the K-9 point of the ring finger is illustrated with longitudinally placed electrodes, electrodes may be placed in either orientation to stimulate either K-9 point. In FIG. 4, a pair of electrodes is shown disposed over the palmar digital nerve on the radial side of the index finger, and a pair of electrodes is shown on the ulnar side of the ring finger, disposed longitudinally over the palmer digital nerve that runs along the ulnar side of the finger. These electrode placements (either singly, or in combination, or applied on the radial and ulnar side to both the ring finger and the index finger) can be used to stimulate the palmar digital nerves rather than the K-9 point.

Figure 6:
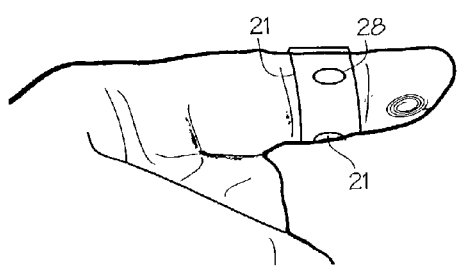
FIG. 6 shows another ring adapted to carry the electrodes used to stimulate the K9 points.
Figure 7:
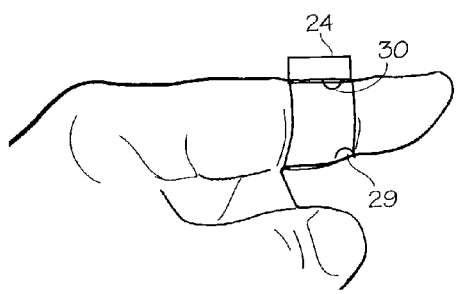
FIG. 7 shows another ring adapted to carry the electrodes used to stimulate the K9 points.
Figure 8:
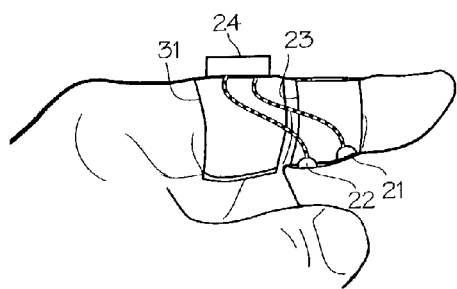
FIG. 8 shows another ring adapted to carry the electrodes used to stimulate the K9 points.

The power source and circuitry necessary for generating and delivering stimulating pulses to the K-9 point through the electrodes may be housed and mounted on the hand or other convenient location in several ways, as illustrated in the following drawings. FIGS. 5 and 6 show similar embodiments of a electroacupuncture stimulation device adapted to be carried on the finger of the patient (either on the index finger, the ring finger, or both). The device comprises a pair of electrodes 21 and 22 disposed on the inner surface of ring or band 23 adapted to fit snugly on the finger. The stimulation power source, pulse generator, and operator controls are mounted inside the housing 24, and conductors 25 and 26 run through the band to connect the pulse generator output to the electrodes. In FIG. 5, the electrodes are arranged longitudinally along the finger, with one electrode placed over the K-9 point or just distal to the K-9 point, and one electrode mounted proximally to the K-9 point. The electrodes are disposed along the midline of the inner surface of the finger. With this electrode placement, current flow is expected to run distally and proximally along the length of the finger. In FIG. 6, the electrodes are arranged laterally, with one electrode 27 placed on the band so that is disposed laterally of the K-9 point and one electrode 28 placed on the band so that it is disposed medially of the K-9 point. In FIG. 7, one electrode 29 is placed on the band so that it overlies the K-9 point, and the other electrode 30 is placed on the band, or on the housing, so that when worn, the electrode is disposed on the outside of the finger, near the third knuckle. While we expect that the distal-to-proximal arrangement will provide optimal stimulation for most patients, the lateral arrangement and palmar-to-dorsal arrangement will also be effective, though perhaps not so universally effective as the distal-to-proximal arrangement. In each of the embodiments shown in FIGS. 5 through 9, the housing can be located immediately over the finger joint which is stimulated, but it can also be located proximally, as shown in FIG. 8, where the housing 24 is located on the first phalange of the finger, mounted on band 31 and electrically connected to the electrodes through flexible connectors 32. Though depicted as a separate bands, bands 23 and 31 may be provided in the form of a single sleeve that extends over the first and second phalanges of the finger.

Figure 9:
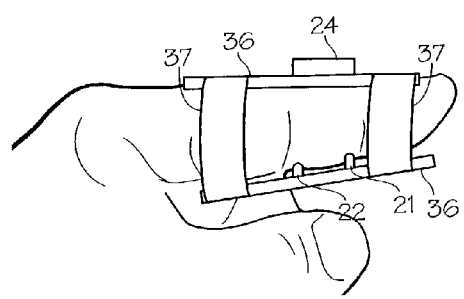
FIG. 9 illustrates finger splint adapted to carry the electrodes used to stimulate the K9 points.

FIG. 9 illustrates an embodiment of the device in which the electrodes are carried by a splint which is adapted to fit over the finger. The splint 36 may be constructed as a typical splint, and may be a two piece splint or a single piece splint. The splint may be taped to the finger or compressed upon the finger with Velcro (hook and loop fastener) straps, elastic strap or an elastic sleeve. In the illustration, the splint is held onto the finger with elastic straps 37. By immobilizing the finger in the extended position, the tissue of the finger pad is stretched, bringing the nerves running through the pad into more superficial location, so that electrical stimulation is more effective, or may be provided at lower power output.

Figure 10:
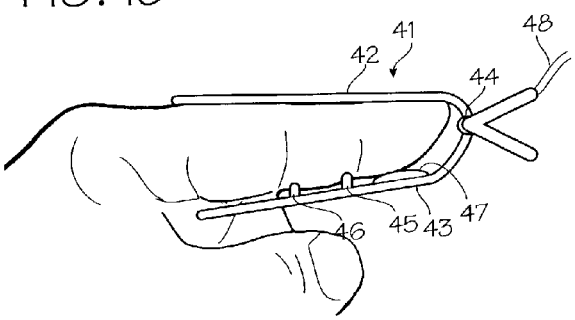
FIG. 10 illustrates finger clip adapted to carry the electrodes used to stimulate the K9 points.

FIG. 10 illustrates a finger clip adapted to carry the electrodes used to stimulate the K9 points. In post-operative settings, where pulse oximeters are often used to monitor the patient, the patient also requires anti-emetic therapy as well. Thus, the pulse oximeter clip can be modified by addition of electrodes and mounting structures to place those electrodes over the K-9 point when the pulse oximeter is installed to place its sensor on the fingertip. The clip 41 includes grasping members 42 and 43 which are hinged about the spring 44, and rotatable relative to each other about the hinge. Stimulation electrodes 45 and 46 are mounted on the palmer grasping member, distanced from the hinge point so that, when placed on the finger, the electrodes span the K-9 point. If the finger clip is provided in the form a stand-alone anti-emetic device, the necessary pulse generation circuitry and power supply can be housed anywhere on the clip. If the device is combined with a pulse oximeter, the pulse oximeter sensor 47 may be located under the finger tip, as usual, and power for the stimulation electrodes can be provided through the same cable 48 that provides power for the pulse oximeter sensor, and pulse generation circuitry can be provided in the same housing used for the pulse oximetry, which is typically separate from the finger clip.

Figure 12:
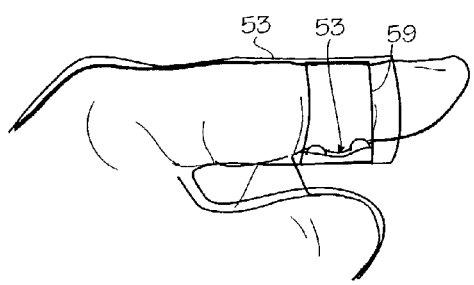
FIG. 12 shows a medial view of the portion of the glove shown in FIG. 11.
Figure 11:
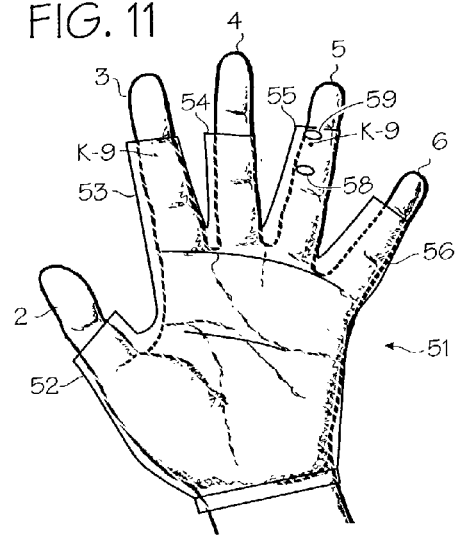
FIG. 11 illustrates a glove adapted to carry the electrodes used to stimulate the K9 points.

FIG. 11 illustrates an embodiment of the anti-nausea device in which the electrodes are mounted on or inside a glove. The glove 51 may be made of any non-conductive material. The glove includes finger sleeves 52, 53, 54, 55, and 56. Electrodes 57 and 58 are disposed over the K-9 point of the index finger, ring finger, or both, and may be provided in distal-to-proximal relationship, lateral relationship, or palmar-dorsal relationship. The electronics and housing can be mounted on the back of the glove, or in an associated housing mounted on the wrist or elsewhere. The sleeve for either the ring finger or index finger may be elastic, if the remainder of the glove is inelastic, to help bias the electrodes against the finger pads. Additionally, the finger sleeves can be fitted with resilient secondary sleeve or non-resilient barrels with an inner diameter and contour which supports the electrodes in position and helps limited displacement of the electrodes during normal wear of the glove. This is illustrated in FIG. 12 which shows a cylindrical foam insert 59 secured within the finger sleeve 53 of the glove. The conformable foam makes up an inner sleeve within the finger sleeve, and this inner sleeve holds the electrodes in place against the pad of the finger. The annular groove of the foam insert accommodates the pad of the finger to help limit longitudinal travel of the electrodes off the desired site.

Figure 13:
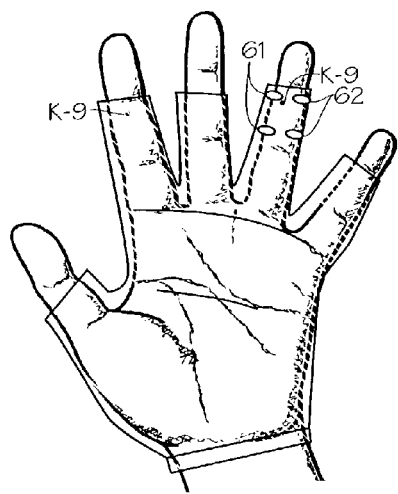
FIGS. 13 through 19 illustrate various electrode placements and configurations that may be used with the ring and glove embodiments described in the previous figures.
Figure 14:
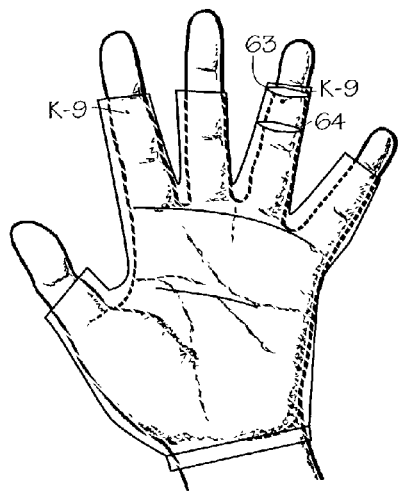
Figure 15:
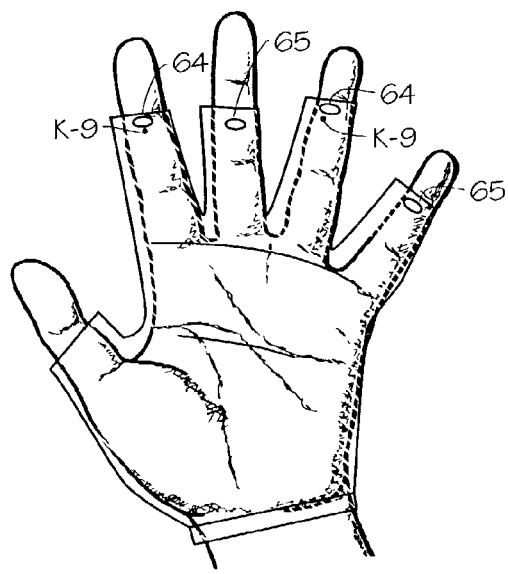
Figure 16:
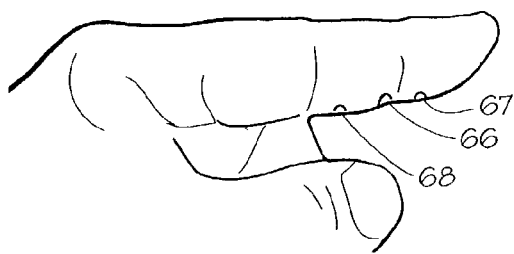
Figure 17:
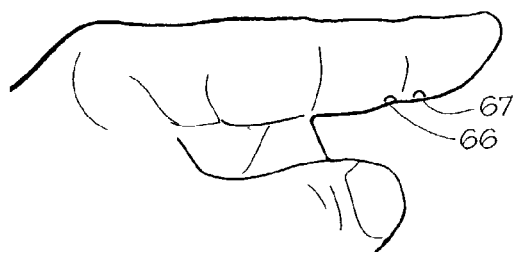
Figure 18:
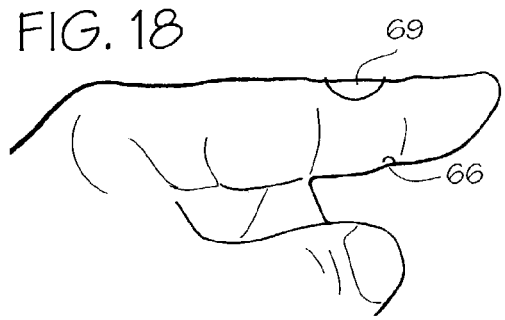
Figure 19:
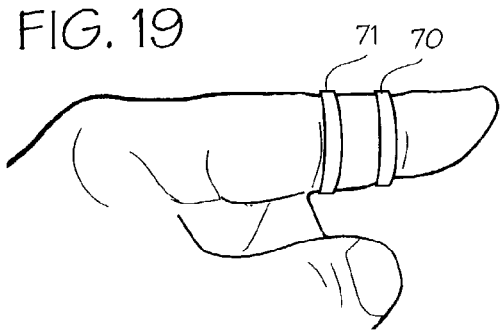

FIGS. 13 through 19 illustrate various alternative positions for the electrodes. FIG. 13 illustrates a glove with two pairs of electrodes 60 and 61, with each pair longitudinally oriented along the finger, disposed over the lateral and medial sides of the finger (overlying the course of the digital nerve). The electrodes are mounted on the glove (or a ring or band) such that, when the glove is fitted onto the hand, the electrodes are positioned as desired. FIG. 14 illustrates a glove with a single pair of electrodes 62 and 63 which are wide relative to the finger, having widths substantially as wide as the finger. Electrodes may be provided in pairs disposed along the palmar pads of the several fingers, with at least one electrode 64 located closely overlying the K-9 point. The other electrode 65 in the bi-polar pair may be located on the middle finger (for the electrode on the index finger) or on the pinky (for the electrode on the ring finger), as illustrated in FIG. 15. Electrode positions may be varied along the finger also. As shown in FIG. 16, one electrode 66 may be located over the K9 point, and two cooperating electrodes 67 and 68 are located on either side, distally and proximally, of the central electrode. These electrodes are operated such that the electrical stimulation is transmitted between the central electrode to both the cooperating electrodes. FIG. 17 shows electrode placement over the K9 point and the distal phalange (the third phalange) of the finger. FIG. 18 illustrates electrode placement where one electrode is placed over the K-9 point and the other electrode is located on the dorsal side of the finger, on the proximal end of the middle phalange. The dorsal electrode 69 in this illustration is quite wide, sized so that it substantially covers the entire width of the dorsal surface of the middle phalange. FIG. 19 illustrates an embodiment of the electrodes in the form of conductive rings 70 and 71 which completely surround, or substantially surround, the middle phalange at the distal and proximal extremities of the phalange.

The ring depicted in the several figures may be a rigid ring, made of plastic or metal (metal construction would require an insulating layer between the finger and the ring), a flexible band or a resilient band. For applications in a clinical or hospital setting, an elastic band may be provided with suitable elasticity so that it fits patients without specific sizing, and just a few sizes should be adequate to fit most patients. The band may provided with an adhesive, like a band-aid, and the device can thereby be taped to the finger. For self-treatment applications in office or social settings, the device can be mounted on rings of standard ring sizes, and the device can be disguised as a ring, ornamented as desired by each wearer. The housing may accordingly be provided in the form of an ornamental housing.

The pulse generation circuitry may be provided as described in our issued U.S. Pat. No. 6,076,018, and many other pulse generation circuits may be used (especially where the circuitry is housed remotely from the stimulation point. The currently preferred pulse pattern comprises approximately 31 pulses per second and a pulse width of 350 microseconds, at a peak current of 10–40 milliamps (depending on the setting) and peak voltage of 5–20 volts (again, depending on the setting) in a 500 ohm load. The waveform is biphasic, meaning that the pulses alternate in polarity. The preferred stimulation pulse may vary as our experience with the device dictates.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A device for treating nausea by electrically stimulating the K9 acupressure point on a finger of a patient's hand, said device comprising:
   a pair of electrodes adapted to contact the fingers in proximity to the K9 point;
   means for mounting the electrodes on the finger and holding them in place in proximity to the K9 point;
   pulse generation circuitry operable attached to the electrodes, said pulse generation circuitry being operable to deliver pulsed electrical stimulation to the finger in the vicinity of the K9 acupressure point through the electrodes; and
   a power source operably connected to the pulse generation circuitry, said finger being selected from the group consisting of the index finger, the ring finger, and the index finger and the ring finger, wherein the means for mounting comprises a splint adapted to be fixed to the finger, and the electrodes are disposed on the splint such that, when the splint is affixed to the patient's finger, the electrodes are disposed in close proximity to the K9 acupressure point.

2. A device for treating nausea by electrically stimulating the K9 acupressure point on a finger of a patient's hand, said device comprising:
   a pair of electrodes adapted to contact the fingers in proximity to the K9 point;
   means for mounting the electrodes on the finger and holding them in place in proximity to the K9 point;
   pulse generation circuitry operable attached to the electrodes, said pulse generation circuitry being operable to deliver pulsed electrical stimulation to the finger in the vicinity of the K9 acupressure point through the electrodes; and
   a power source operably connected to the pulse generation circuitry, said finger being selected from the group consisting of the index finger, the ring finger, and the index finger and the ring finger, wherein the means for mounting comprises a finger clip adapted to be fixed to the finger, and comprises a finger clip adapted to be fixed to the finger, and the electrodes are disposed on the finger clip such that, when the splint is affixed to the patient's finger, the electrodes are disposed in close proximity to the K9 acupressure point.

3. A device for treating nausea by electrically stimulating the K9 acupressure point on a finger of a patient's hand, said device comprising:
   a pair of electrodes adapted to contact the fingers in proximity to the K9 point;
   means for mounting the electrodes on the finger and holding them in place in proximity to the K9 point;
   pulse generation circuitry operable attached to the electrodes, said pulse generation circuitry being operable to deliver pulsed electrical stimulation to the finger in the vicinity of the K9 acupressure point through the electrodes; and
   a power source operably connected to the pulse generation circuitry, said finger being selected from the group consisting of the index finger, the ring finger, and the index finger and the ring finger, wherein the means for mounting comprises a pulse oximeter clip adapted to be fixed to the finger, and the electrodes are disposed on the pulse oximeter monitor clip such that, when the pulse oximeter clip is affixed to the patient's finger to measure the patient's blood oxygen content, the electrodes are disposed in close proximity to the K9 acupressure point.

4. A device for treating nausea by electrically stimulating the K9 acupressure point on a finger of a patient's hand, said device comprising:
   a pair of electrodes adapted to contact the fingers in proximity to the K9 point;
   means for mounting the electrodes on the finger and holding them in place in proximity to the K9 point;
   pulse generation circuitry operable attached to the electrodes, said pulse generation circuitry being operable to deliver pulsed electrical stimulation to the finger in the vicinity of the K9 acupressure point through the electrodes; and
   a power source operably connected to the pulse generation circuitry, said finger being selected from the group consisting of the index finger, the ring finger, and the index finger and the ring finger, wherein the means for mounting comprises a glove be fixed on the patient's hand, said glove comprising at least one finger sleeve adapted to be fitted over a K9 point of the patient, and the electrodes are disposed on the sleeve such that, when the glove is fitted onto the patient's hand and sleeve is fitted over a K9 point, the electrodes are disposed in close proximity to the K9 acupressure point.

5. The device of claim 1, 2, 3, or 4 wherein the electrodes are disposed on the mounting means so that, when the mounting means is fitted onto the patient, the electrodes are disposed longitudinally along the middle phalange of the finger.

6. The device of claim 1, 2, 3, or 4 wherein the pair of electrodes is disposed on the mounting means so that, when the mounting means is fitted onto the patient, one electrode is disposed on the lateral side of the finger and the other electrode is disposed on the medial side of the finger.

7. The device of claim 1, 2, 3, or 4 wherein the pair of electrodes is disposed on the mounting means so that, when the mounting means is fitted onto the patient, the electrodes are disposed longitudinally along the middle phalange of the finger, and disposed off-center on the finger so as to overly a digital nerve.

* * * * *